Figure 1:
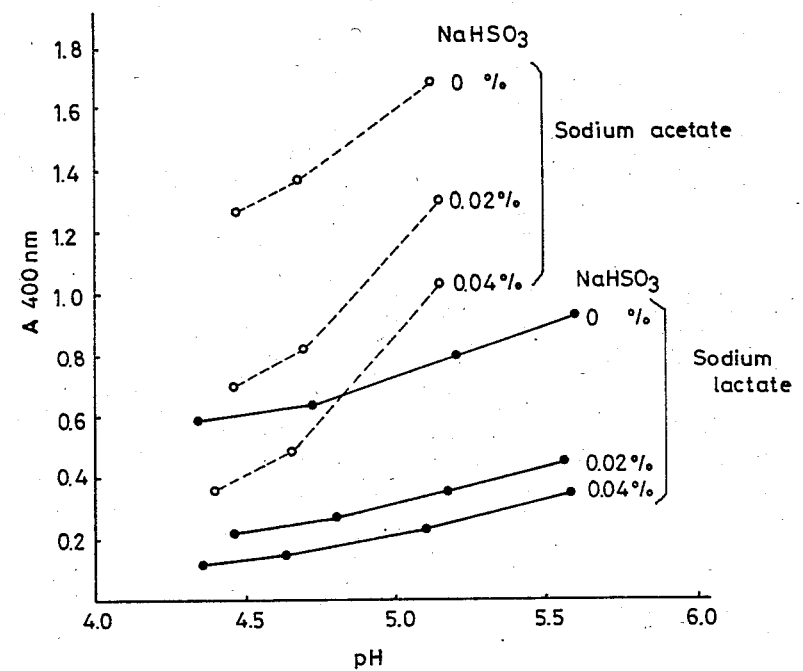

United States Patent [19]

Kawajiri

[11] Patent Number: 4,604,286

[45] Date of Patent: Aug. 5, 1986

[54] INFUSION SOLUTION FOR PARENTERAL NUTRITION

[75] Inventor: Seizo Kawajiri, Nagaokakyo, Japan

[73] Assignee: Daigo Nutritive Chemicals, Ltd., Osaka, Japan

[21] Appl. No.: 652,221

[22] Filed: Sep. 17, 1984

[51] Int. Cl.$^4$ .................. A61K 31/70; A61K 31/195; A61K 33/06; A61K 33/14; A61K 33/20

[52] U.S. Cl. .................................... 424/149; 424/153; 424/154; 514/23; 514/561

[58] Field of Search ............... 424/153, 154, 319, 149; 514/23, 561

[56] References Cited

U.S. PATENT DOCUMENTS

| | | | |
|---|---|---|---|
| 3,773,930 | 11/1973 | Mohammed et al. | 424/19 |
| 4,025,650 | 5/1977 | Gans et al. | 424/19 |
| 4,279,917 | 7/1984 | Takami et al. | 424/19 |
| 4,368,204 | 1/1983 | Sato et al. | 424/19 |

OTHER PUBLICATIONS

Physician's Desk Reference, (1974) 28th ed. p. 1257.

*Primary Examiner*—Stanley J. Friedman
*Attorney, Agent, or Firm*—Wenderoth, Lind & Ponack

[57] ABSTRACT

Infusion solutions for parenteral nutrition which contain amino acids, dextrose and electrolytes.

3 Claims, 1 Drawing Figure

INFUSION SOLUTION FOR PARENTERAL NUTRITION

The present invention relates to an infusion solution for parenteral nutrition containing dextrose, amino acids and electrolytes.

It is known that an infusion solution for the total parenteral nutrition should contain dextrose, amino acids and electrolytes. For amino acids, it is essential to use essential amino acids such as isoleucine, leucine, methionine phenylalanine, threonine, valine, tryptophane and lysine. In addition thereto there may be used one or more of arginine, histidine, aspartic acid, glutamic acid, alanine, cystine, aminoacetic acid, proline, serine and thyrosine. As for the electrolytes there have been used those which can provide ions of potassium, sodium, magnesium, calcium, phosphate and chlorine. Generally these electrolytes are in the form of chlorides, sulfates, phosphates and organic acid salts.

However there has been encountered with difficulty for an infusion solution containing dextrose, amino acids and electrolytes at the same time. Thus such solution is unstable and, particularly, coloration occurs upon its sterilization and storage. Therefore it has been conventional to prepare two separate solutions i.e. one containing dextrose and the other containing amino acids (the electrolytes may be added to either one or both of these separate solutions), and the two separate solutions are mixed together just prior to the administration to patients. If it were possible to prepare a stable single solution containing dextrose, amino acids and electrolytes at the same time there should be advantages, for example, that a troublesome operation for mixing two separate solutions in advance to administration is avoided and possibility of bacterial contamination or the like at the time of mixing the two solutions is reduced.

The serious problem of the single infusion solution preparation containing dextrose, amino acids and electrolytes at the same time is that the solution is unstable as mentioned before. Thus in such solution there occurs a browning reaction (Maillard reaction) between dextrose and amino acids, resulting in undesirable coloration. The coloration becomes more remarkable when the infusion solution is heated (or steamed) for sterilization and also upon storage.

In view of the above we have conducted research to overcome the above mentioned problem and have found that the undesirable coloration of an infusion solution containing dextrose, amino acids and electrolytes depends upon the pH of the solution (the higher the pH the more the coloration), that the coloration is also affected by the particular kind of organic acid used and further that, among organic acids, lactate causes substantially no coloration.

Thus the present invention provides an infusion solution for parenteral nutrition containing dextrose, amino acids and electrolytes in the form of salts with acids, characterized in that the said acids are hydrochloric acid, phosphoric acid and lactic acid and that the pH of the solution is 4.5–5.5 as adjusted with lactic acid and/or phosphoric acid and/or hydrochloric acid and/or sulfuric acid, the total amount of each of these acids in the solution being within a certain range.

In the present invention the solution contains 3–10 W/V %, preferably 5–7.5 W/V % of dextrose or glucose which is well known in the art of parenteral solution.

The kinds of amino acids and concentrations thereof in the infusion solution according to this invention may be those known in the art and may vary depending upon the particular purpose of administration. Generally, however, the use of the following amino acids and concentrations thereof are recommended.

TABLE I

| Amino acid | Concentration (g/l) | |
|---|---|---|
| | Possible range | Preferable range |
| L-Methionine | 1.09–3.27 | 1.64–2.18 |
| L-Isoleucine | 1.61–4.83 | 2.42–3.22 |
| L-Leucine | 2.02–6.06 | 3.03–4.04 |
| L-Phenylalanine | 1.12–3.36 | 1.68–2.24 |
| L-Valine | 1.45–4.35 | 2.17–2.90 |
| L-Threonine | 0.81–2.43 | 1.22–1.62 |
| L-Lysine.HCl | 1.46–4.38 | 2.19–2.92 |
| L-Tryptophan | 0.32–0.96 | 0.48–0.64 |
| L-Alanine | 0–4.59 | 2.29–3.06 |
| L-Arginine | 0–5.76 | 2.88–3.84 |
| L-Histidine | 0–1.74 | 0.87–1.16 |
| L-Proline | 0–6.78 | 3.39–4.52 |
| L-Serine | 0–3.60 | 1.80–2.40 |
| Amino acetic acid | 0–7.80 | 3.90–5.20 |
| L-Cysteine.HCl | 0–0.09 | 0.04–0.06 |

One of the important features of the present invention is in the particular composition of the electrolytes, particularly acid components to form the electrolytes and for the pH adjustment to be explained hereinlater. Thus, as is known in the art, an infusion solution for parenteral nutrition of this kind should contain, in addition to dextrose and amino acid, adequate amounts of certain electrolytes i.e. compounds providing ions of sodium potassium, magnesium, calcium, phosphate and chlorine in the aqueous infusion solution. These compounds are used in the form of salts with acids. However useful acids are limited because many acids are pharmacologically unacceptable to the patient. Therefore as for inorganic acids there have been used hydrochloric acid, phosphoric acid and sulfuric acid. However the concentrations of these acid which are allowed to be present in the infusion solution are limited since these acids are not metabolizable and unduly large amounts of these inorganic acids would cause acidosis and undesirable side effects. Therefore it has been impossible to use these inorganic acids in the quantities necessary to maintain sufficient amounts of sodium, potassium, magnesium, calcium and phosphate ions in the solution and to effect the desirable pH adjustment. Therefore it has been inevitable to employ a metabolizable organic acid at least as a portion of the acids for forming the electrolytes and/or for the pH adjustment. However, the problem encountered with the use of such organic acid is that there would be caused undesirable browing effect due to the Maillard reaction between glucose and amino acids as mentioned before.

We have found that the various troublesome problems are solved by using lactic acid and not any other organic acid. Thus, according to the present invention, the electrolytes should have a composition within the following range:

TABLE II

| Ions | Concentration m Eq/l |
|---|---|
| Na+ | 30–60* |
| K+ | 20–35* |
| Mg++ | 0–5 |

TABLE II-continued

| Ions | Concentration m Eq/l |
|---|---|
| $Ca^{++}$ | 0–5 |
| $HPO_4^{--}$ | 0–10 |
| $Cl^-$ | 30–70** |
| $SO_4^{--}$ | 0–5 |
| $C_3H_5O_3^-$ | 10–50 |

*The amount of sodium and potassium includes those contained in any stabilizer to be explained hereinafter.
**The amount of chlorine includes that of hydrochloride of the amino acid(s) used.

More particular examples of the electrolytes in the form of metal salts are NaCl, $NaC_3H_5O_3$, $NaH_2PO_4$, $Na_2HPO_4$, KCl, $KC_3H_5O_3$, $KH_2PO_4$, $K_2HPO_4$, $MgCl_2$, $MgSO_4$, $Mg(C_3H_5O_3)_2$, $CaCl_2$, $Ca(C_3H_5O_3)_2$, etc.

As mentioned above the important feature of the present invention is in that no organic acid should be used other than lactic acid.

Another important feature of the present invention is to adjust the pH of the solution to 4.5–5.5 and that, for the pH adjustment, there is used no organic acid other than lactic acid. Thus the pH adjustment is effected with the use of one or more of hydrochloric acid, phosphoric acid, sulfuric acid and lactic acid. The kind and amount of the acid(s) to be used for the pH adjustment must be selected so as to satisfy the composition ranges specified in the above TABLE II. By taking these special measures for the pH adjustment the occurrence of the undesirable blowing reaction may be further diminished.

If desired the infusion solution of the present invention may further contain a stabilizer (antioxidant) known for infusion solutions of this kind. The stabilizer to be used is selected from the group consisting of $NaHSO_3$, $Na_2S_2O_5$, $Na_2SO_3$, $KHSO_3$, $K_2S_2O_5$ and $K_2SO_3$. The amount of the stabilizer may be 0.06 W/V % or less, preferably 0.04–0.05 W/V % based on the infusion aqueous solution. However, here again, the amount of the stabilizer should be that satisfying the proportions defined in TABLE II in respect of Na and/or K ion concentration.

By the use of these ingredients, infusion solutions may be prepared in the usual manner. Thus dextrose, amino acids and electrolytes (and stabilizer if any) are dissolved in distilled water for injection and the pH is adjusted to 4.5–5.5. The solution is packed in a proper container and then sterilized in a manner well known in the art.

The present invention will be further explained below by referring partly to the accompanying drawing wherein FIG. 1 is a graph to show how the degree coloration of the infusion solution is affected by the particular kind of the organic salt (acetate vs. lactate), pH and the addition of $NaHSO_3$.

When aqueous solutions of three kinds of compositions shown in TABLE III below were sealed in ampoules under nitrogen gas replacement and were heated at 100° C. for 30 or 60 minutes. With the compositions A and B, the solutions were colored yellow to brown. The color intensity may be represented by an absorbance at 400 nm. The composition C in which dextrose was not contained was not substantially colored even when heated. However in case of the compositions A and B in which both dextrose and amino acids are contained at the same time, there occurred substantial coloration. The coloration was more remarkable in case of the composition A which also contains electrolytes.

TABLE III

| | Concentrations (W/V %) | | |
|---|---|---|---|
| Components | A | B | C |
| Dextrose | 18.7 | 18.7 | — |
| Amino acids* | 4 | 4 | 4 |
| Sodium chloride | 0.0292 | — | 0.0292 |
| Sodium acetate | 0.61 | — | 0.61 |
| Monopotassium phosphate | 0.0817 | — | 0.0817 |
| Magnesium sulfate | 0.1027 | — | 0.1027 |
| Calcium chloride | 0.058 | — | 0.058 |
| Acid sodium sulfite | 0.02 | 0.02 | 0.02 |
| pH | 5.3 | 5.42 | 6.0 |
| A 400 nm after heating at 100° C. for 30 minutes | 0.19 | 0.04 | 0.01 |
| A 400 nm after heating at 100° C. for 60 minutes | 1.12 | 0.15 | 0.02 |

*L-isoleucine 0.28, leucine 0.39, lysine hydrochloride 0.34, methionine 0.18, phenylalanine 0.43, threonine 0.2, tryptophane 0.072, valine 0.29, arginine hydrochloride 0.4, histidine hydrochloride 0.2, aspartic acid 0.2, glutamic acid 0.06, alanine 0.16, cystine 0.008, aminoacetic acid 0.61, proline 0.08, serine 0.08, thyrosine 0.02 (W/V %).

Further, as apparent from TABLE IV, in case the pH of the composition A in TABLE III was varied with hydrochloric acid or sodium hydrochloride, the higher the pH, the larger the coloring after heating.

TABLE IV

| | A 400 nm after heating | |
|---|---|---|
| pH | at 100° C. for 30 minutes | at 100° C. for 60 minutes |
| 4.8 | 0.08 | 0.34 |
| 5.2 | 0.15 | 0.84 |
| 5.8 | 0.32 | 1.6 |

Further, in the above composition A the concentration of sodium acetate was varied and the solution was heated at 100° C. The results are shown in TABLE V, from which it has been observed that the degree of coloring depends also upon the concentration of sodium acetate in the solution.

TABLE V

| | A 400 nm after heating | |
|---|---|---|
| | at 100° C. for 30 minutes | at 100° C. for 60 minutes |
| Concentration of sodium acetate (% by weight) | | |
| 0.3 | 0.14 | 0.54 |
| 0.61 | 0.21 | 0.84 |
| 1.22 | 0.27 | 1.08 |
| Composition (W/V %) | | |
| Dextrose | 18.7 | |
| Amino acid group* | 4 | |
| Sodium chloride | 0.0292 | |
| Sodium acetate | 0.3, 0.61, 1.22 | |
| Monopotassium phosphate | 0.0817 | |
| Magnesium sulfate | 0.1027 | |
| Calcium chloride | 0.058 | |
| Hydrochloric acid | Proper amount | |
| pH | 4.6 | |

*Same as those in TABLE III.

Even if the concentrations of other electrolytes were varied, the intensity of the coloring did not vary and the coloration degree was the same.

From these results, it has been observed that the coloring of the composition A is caused by the reaction between dextrose and amino acids and the coloration is promoted by sodium acetate.

Then, experiments have been conducted to determine the influence by the kind of organic acid salt on the coloration reaction between dextrose and amino acids. The results are shown in TABLE VI. It has been observed therefrom that the coloring degree is greatly affected depending on the kind of the organic acid salt and, among the tested organic acid salts, the lactate has the least influence and the citrate has the greatest influence.

TABLE VI

|  | A 400 nm after heating at 100° C. for 60 minutes |
|---|---|
| added organic acid salts |  |
| none | 0.18 |
| Sodium acetate | 0.75 |
| Sodium succinate | 1.10 |
| Sodium lactate | 0.20 |
| Sodium maliate | 0.74 |
| Sodium citrate | 1.24 |
| Sodium tartrate | 0.70 |
| Sodium fumarate | 0.72 |
| Sodium malonate | 0.90 |
| Sodium oxalate | 0.94 |
| Composition |  |
| Dextrose | 18.7 W/V % |
| Aminoacetic acid | 2.4 W/V % |
| Organic acid salt | 0.0744 mol/l |
| Hydrochloric acid | Proper amount |
| pH | 5.0 |
| Ampoule space | Nitrogen |

FIG. 1 is a graph showing the relations between the coloration degree and pH and the influences of the addition of acid sodium sulfite. Thus an aqueous solution having the following composition was prepared.

| Dextrose | 18.7 W/V % |
|---|---|
| Amino acid group* | 4 |
| Sodium chloride | 0.0346 |
| Monopotassium phosphate | 0.082 |
| Magnesium sulfate | 0.103 |
| Calcium chloride | 0.058 |
| Sodium acetate or sodium lactate | 0.0756 mol/l |
| Acid sodium sulfite | 0; 0.02; 0.04% |
| Hydrochloric acid | Proper amount |
| Ampoule space | Nitrogen |

*Same as those in TABLE III.

The solution was heated at 100° C. for 60 minutes. It has been found from the graph that the addition of acid sodium sulfite has an effect of further reducing the degree of coloration. It has also been observed that the effect of lactate is more remarkable when the pH of the solution is higher.

When the pH of an infusion solution containing dextrose, amino acids, and electrolytes is lower than the pH range shown in FIG. 1, that is, lower than a pH of 4.5, the coloring degree will be less. However, on the other hand, the buffering of the solution will be stronger, and therefore, such solution (which is usually administered in a large amount) would be not preferable for infusion to living body. Further, the higher the pH, the more likely the coloring. Therefore, it would be necessary to adjust the pH of the solution to 4.5 to 5.5.

The manner of administration and dosage of the intravenous solutions of the present invention are known per se and do not constitute a part of the invention so that no detailed explanation thereabout will be required.

The invention will be illustrated in the following Examples which are not to limit the scope of the invention.

EXAMPLE 1

In 700 ml of sterile distilled water for injection there were dissolved the following ingredients:

| Dextrose | 70 g | L-Serine | 1.9 g |
|---|---|---|---|
| L-Methionine | 1.6 g | Amino acetic acid | 4.0 g |
| L-Isoleucine | 2.5 g | L-Tryptophan | 0.5 g |
| L-Leucine | 3.1 g | L-Cysteine.HCl | 0.05 g |
| L-Phenylalanine | 1.7 g | NaCl | 1.59 g |
| L-Valine | 2.3 g | KCl | 0.73 g |
| L-Threonine | 1.3 g | K$_2$HPO$_4$ | 0.87 g |
| L-Lysine.HCl | 2.4 g | Ca(C$_3$H$_5$O$_3$)$_2$.5H$_2$O | 0.46 g |
| L-Alanine | 2.4 g | MgSO$_4$.7H$_2$O | 0.37 g |
| L-Arginine | 3.0 g | NaHSO$_3$ | 0.5 g |
| L-Histidine | 1.0 g |  |  |
| L-Proline | 3.4 g |  |  |

To the solution was added 10% lactic acid to adjust the pH to 4.8. An additional amount of sterile distilled water was added so as to make 1000 ml solution. The solution was filtered through a Millipore filter and packed into a 500 ml vial for infusion solution. The space was replaced by nitrogen gas and the vial was sealed with a rubber plug, and then subjected to steam sterilization under USP XX standard method. The sterilized infusion solution was colorless and transparent. No coloring was observed even upon storage at room temperature for 6 months.

For comparison the same procedure was repeated except that the pH adjustment was effected by the use of 10% acetic acid instead of 10% lactic acid. Upon the steam sterilization the solution was yellow colored. Upon storage the color became deeper to brown.

EXAMPLE 2

In 700 ml of sterile distilled water for injection there were dissolved the following ingredients.

| Dextrose | 50 g | L-Serine | 1.9 g |
|---|---|---|---|
| L-Methionine | 1.6 g | Amino acetic acid | 4.0 g |
| L-Isoleucine | 2.5 g | L-Tryptophan | 0.5 g |
| L-Leucine | 3.1 g | L-Cysteine.HCl | 0.05 g |
| L-Phenylalanine | 1.7 g | NaCl | 0.93 g |
| L-Valine | 2.3 g | NaC$_3$H$_5$O$_3$ | 1.04 g |
| L-Threonine | 1.3 g | KCl | 1.04 g |
| L-Lysine.HCl | 2.4 g | K$_2$HPO$_4$ | 0.52 g |
| L-Alanine | 2.4 g | Ca(C$_3$H$_5$O$_3$)$_2$.5H$_2$O | 0.41 g |
| L-Arginine | 3.0 g | MgSO$_4$.7H$_2$O | 0.37 g |
| L-Histidine | 1.0 g | NaHSO$_3$ | 0.5 g |
| L-Proline | 3.4 g |  |  |

To the solution was added 10% lactic acid to adjust the pH to 5. An additional amount of distilled sterile water was added so as to make 1000 ml solution. The solution was treated in the same manner as in Example 1 to obtain a colorless transparent infusion solution. Even upon storage at room temperature for 6 months no coloring was observed.

For comparison the same procedure was repeated except that the potassium lactate and calcium lactate were replaced respectively with 1.26 g of sodium acetate (trihydrate) and 0.23 g of calcium acetate (monohydrate) and that the pH adjustment was effected by the use of 10% acetic acid instead of 10% lactic acid. Upon the steam sterilization the solution was yellow colored.

EXAMPLE 3

In 700 ml of sterile distilled water for injection there were dissolved the following ingredients.

| | | | |
|---|---|---|---|
| Dextrose | 50 g | L-Serine | 1.5 g |
| L-Methionine | 1.7 g | Amino acetic acid | 3.5 g |
| L-Isoleucine | 2.5 g | L-Tryptophan | 0.5 g |
| L-Leucine | 3.5 g | NaCl | 0.18 g |
| L-Phenylalanine | 2.2 g | NaC$_3$H$_5$O$_3$ | 3.05 g |
| L-Valine | 2.6 g | KCl | 1.49 g |
| L-Threonine | 1.6 g | K$_2$HPO$_4$ | 0.44 g |
| L-Lysine.HCl | 2.2 g | CaCl$_2$.2H$_2$O | 0.37 g |
| L-Alanine | 2.3 g | MgSO$_4$ | 0.37 g |
| L-Arginine | 2.7 g | NaHSO$_3$ | 0.5 g |
| L-Histidine | 1.0 g | | |
| L-Proline | 3.0 g | | |

To the solution was added N-hydrochloric acid to adjust the pH to 5.3. An additional amount of distilled sterile water was added to make 1000 ml solution. The solution was treated in the same manner as in Example 1 to obtain a colorless transparent infusion solution. Even upon storage at room temperature for 6 months no coloring was observed.

For comparison the above procedure was repeated except that sodium lactate was replaced with 3.7 g of sodium acetate (trihydrate). Upon the steam sterilization the solution was yellow colored.

In the above Examples 1, 2 and 3 the concentrations (as m Eq/1) of the various electrolytes contained in the respective final infusion solutions were as follows.

| | Example 1 | Example 2 | Example 3 |
|---|---|---|---|
| Na$^+$ | 31.9 | 30 | 35 |
| K$^+$ | 19.8 | 20 | 25 |
| Mg$^{++}$ | 3 | 3 | 3 |
| Ca$^{++}$ | 3 | 2.7 | 5 |
| Cl$^-$ | 50 | 43 | ca 50 |
| HPO$_4^{--}$ | 10 | 6 | 5 |
| SO$_4^{--}$ | 3 | 3 | 3 |
| C$_3$H$_5$O$_3^-$ | ca 25 | ca 35 | 27.2 |

What is claimed is:

1. An aqueous infusion solution for parenteral nutrition containing dextrose, amino acids and electrolytes in the form of salts of sodium, potassium, magnesium, calcium, phosphate and chlorine in the solution, wherein the pH of the solution is 4.5–5.5,
said compounds being in the form of salts with hydrochloric acid, phosphoric acid, sulfuric acid and latic acid,
the pH adjustment is effected by the use of an acid selected from the group consisting of hydrochloric acid, phosphoric acid, sulfuric acid and lactic acid,
the content of dextrose is 3–10 W/V %,
the content of amino acids is as follows:

| Amino acid | Concentration (g/l) |
|---|---|
| L-Methionine | 1.09–3.27 |
| L-Isoleucine | 1.61–4.83 |
| L-Leucine | 2.02–6.06 |
| L-Phenylalanine | 1.12–3.36 |
| L-Valine | 1.45–4.35 |
| L-Threonine | 0.81–2.43 |
| L-Lysine.HCl | 1.46–4.38 |
| L-Tryptophan | 0.32–0.96 |
| L-Alanine | 0–4.59 |
| L-Arginine | 0–5.76 |
| L-Histidine | 0–1.74 |
| L-Proline | 0–6.78 |
| L-Serine | 0–3.60 |
| Amino acetic acid | 0–7.80 |
| L-Cysteine HCl | 0.0.09 | and
the concentrations (as mEq/1) of the electrolytes including the acids used for the pH adjustment and f the hydrochlorides, if any, of the amino acid(s) are as follows:

| | |
|---|---|
| Na$^+$ | 30–60 |
| K$^+$ | 20–35 |
| Mg$^+$ | 0–5 |
| Ca$^{++}$ | 0–5 |
| HPO$_4^{--}$ | 0–10 |
| Cl$^-$ | 30–70 |
| SO$_4^{--}$ | 0–5 | and said solution further containing at least one of sodium lactate, calcium lactate or lactic acid in a concentration of 10–50 mEq/1 and said solution being free from any organic acid or its salt other than lactic acid or is salt.

2. The aqueous solution according to claim 1 wherein the content of amino acids is as follows:

| Amino Acid | Concentration (g/l) |
|---|---|
| L-Methionine | 1.64–2.18 |
| L-Isoleucine | 2.42–3.22 |
| L-Leucine | 3.03–4.04 |
| L-Phenylalanine | 1.68–2.24 |
| L-Valine | 2.17–2.90 |
| L-Threonine | 1.22–1.62 |
| L-Lysine.HCl | 2.19–2.92 |
| L-Tryptophan | 0.48–0.64 |
| L-Alanine | 2.29–3.06 |
| L-Arginine | 2.88–3.84 |
| L-Histidine | 0.87–1.16 |
| L-Proline | 3.39–4.52 |
| L-Serine | 1.80–2.40 |
| Amino acetic acid | 3.90–5.20 |
| L-Cysteine.HCl | 0.04–0.06 |

3. The aqueous solution according to claim 1 which further contains a stabilizer selected from the group consisting of NaHSO$_3$, Na$_2$S$_2$O$_5$, Na$_2$SO$_3$, KHSO$_3$, K$_2$S$_2$O$_5$ and K$_2$SO$_3$ in an amount of up to 0.04 to 0.05 W/V %.

* * * * *